United States Patent

Wüthrich

Patent Number: 5,141,951
Date of Patent: Aug. 25, 1992

[54] 5-PHENYL-1H-PYRAZOL-4-PROPIONIC ACID DERIVATIVES, COMPOSITIONS AND USE

[75] Inventor: Hans-Jürg Wüthrich, Kehrsatz, Switzerland

[73] Assignee: Sandoz Ltd., Basel, Switzerland

[21] Appl. No.: 800,781

[22] Filed: Nov. 27, 1991 (Under 37 CFR 1.47)

Related U.S. Application Data

[63] Continuation of Ser. No. 733,496, Jul. 22, 1991, abandoned, which is a continuation of Ser. No. 666,175, Mar. 7, 1991, abandoned.

[30] Foreign Application Priority Data

Mar. 6, 1990 [GB] United Kingdom ............... 9005028

[51] Int. Cl.⁵ .................. A61K 31/415; C07D 231/12
[52] U.S. Cl. .................................. 514/406; 514/826; 514/863; 514/886; 514/887; 548/378
[58] Field of Search ......................... 548/378; 514/406

[56] References Cited

U.S. PATENT DOCUMENTS 4,146,721  3/1979  Rainer ................................. 548/378

Primary Examiner—Robert W. Ramsuer
Attorney, Agent, or Firm—Gerald D. Sharkin; Robert S. Honor; Thomas O. McGovern

[57] ABSTRACT

Compounds of formula I

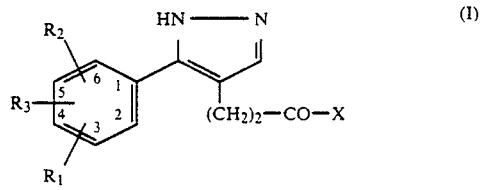

wherein
$R_1$ is alkyl, alkoxy, alkylthio, alkylamino, aryl, aryloxy, arylthio, arylamino, aralkyl, aralkoxy, aralkylthio or aralkylamino,
$R_2$ and $R_3$ are each independently hydrogen, halogen, hydroxy, mercapto, nitro or amino or have the meanings given for $R_1$, and
X is $-NH_2$, $-NH-OH$, $-N(R_4)OH$, $-NH-NH_2$ or $-NH-N=C(R_4)R_5$, wherein
$R_4$ and $R_5$ are each alkyl,
in free form or pharmaceutically acceptable salt form, have pharmaceutical utility, in particular in the treatment or prophylaxis of asthma, or in the treatment of inflammation or psoriasis.

11 Claims, No Drawings

5-PHENYL-1H-PYRAZOL-4-PROPIONIC ACID DERIVATIVES, COMPOSITIONS AND USE

This is a continuation of application Ser. No. 07/733,496, filed Jul. 22, 1991, now abandoned which in turn is a continuation of application Ser. No. 07/666,175, filed Mar. 7, 1991, now abandoned.

The present invention relates to novel 5-phenyl-1H-pyrazol-4-propionic acid derivatives having valuable pharmaceutical properties and processes for their production, as well as pharmaceutical compositions comprising said propionic acid derivatives and their use as pharmaceuticals.

More particularly the present invention provides a compound of formula I

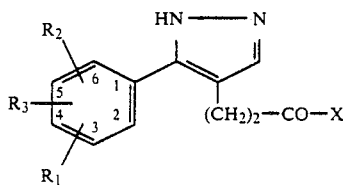

(I)

wherein
- $R_1$ is alkyl, alkoxy, alkylthio, alkylamino, aryl, aryloxy, arylthio, arylamino, aralkyl, aralkoxy, aralkylthio or aralkylamino,
- $R_2$ and $R_3$ are each independently hydrogen, halogen, hydroxy, mercapto, nitro or amino or have the meanings given for $R_1$, and
- X is $-NH_2$, $-NH-OH$, $-N(R_4)OH$, $-NH-NH_2$ or $-NH-N=C(R_4)R_5$, wherein
- $R_4$ and $R_5$ are each alkyl, or acid addition salt thereof.

Alkyl groups as $R_1$, $R_2$, $R_3$, $R_4$ and $R_5$ as well as alkoxy, alkylthio and alkylamino groups and alkyl moieties or aralkyl, aralkoxy, aralkylthio and aralkylamino groups as $R_1$, $R_2$ and $R_3$ may be branched or straight-chained.

Alkyl groups as $R_1$ are preferably $(C_{1-12})$alkyl. Preferably they have a chain length of at least 4 carbon atoms. Suitably they contain maximally 20, more suitably maximally 15 carbon atoms in toto. Most preferably they are straight-chain $C_{4-12}$alkyl.

Alkoxy, alkylthio and alkylamino groups as $R_1$ preferably have 1 to 12 carbon atoms. Preferably they have a chain length of at least 3 carbon atoms. Preferably they have a chain length of at most 11 carbon atoms. Suitably they comprise maximally 20, more suitably maximally 15 carbon atoms in toto. Most preferably they are straight-chain $C_{3-11}$alkoxy, $C_{3-11}$alkylthio or $C_{3-11}$alkylamino.

Alkyl, alkoxy, alkylthio and alkylamino groups as $R_2$ and $R_3$ preferably comprise 1 to 5 carbon atoms.

Aryl groups as $R_1$, $R_2$ and $R_3$ as well as aryl moieties of substituents $R_1$, $R_2$ and $R_3$ are, e.g. phenyl. Such groups may be further substituted if desired.

Alkyl moieties of aralkyl, aralkoxy, aralkylthio and aralkylamino groups as $R_1$, $R_2$ and $R_3$ suitably comprise 1 to 4 carbon atoms, preferred groups being phenyl-$(C_{1-4}$alkyl), phenyl-$(C_{1-4}$alkoxy), phenyl-$(C_{1-4}$alkylthio) and phenyl-$(C_{1-4}$alkylamino).

Alkyl groups as $R_4$ and $R_5$ are preferably $C_{1-4}$alkyl.

By halogen is meant fluorine, chlorine, bromine or iodine.

In the compounds of formula I, the following significances are preferred either individually or in any combination or subcombination:
- $R_1$ is $C_{1-12}$alkyl, $C_{1-12}$alkoxy, $C_{1-12}$alkylthio, phenyl or phenoxy;
- $R_2$ and $R_3$ are each independently hydrogen, hydroxy or $C_{1-4}$alkoxy;
- $R_4$ and $R_5$ are each $C_{1-4}$alkyl;
- X is other than $NH_2$;
- $R_1$ is preferably in the 4-position;
- $R_2$ and $R_3$ are suitably in the 2-position/3-position.

The compounds of the invention may exist in free or acid addition salt form.

As will be appreciated the compounds of the invention may also exist in the form of the tautomers of formula (Ia)

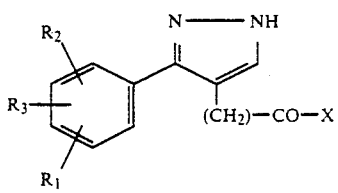

(Ia)

For the sake of convenience the compounds of the invention are defined throughout the present specification and claims by reference to the formula I structure. The present invention is however to be understood as embracing both individual isomers of formula I and Ia as well as mixtures thereof.

In addition to the foregoing the present invention also provides a process for the production of compounds of formula I and their acid addition salts which process comprises:

a) for the production of a compound of formula I wherein X is $-NH_2$, $-NH-OH$, $-N(R_4)OH$ or $-NHNH_2$, reacting a compound of formula II

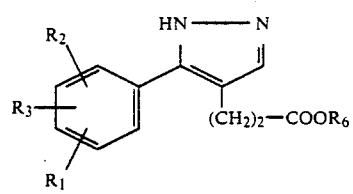

(II)

wherein $R_6$ is hydrogen or $C_{1-4}$alkyl and $R_1$, $R_2$ and $R_3$ have the meanings given for formula I except that hydroxy, mercapto or amino groups as $R_2$ and $R_3$ may be in either free or protected form, with a compound of formula H—X' wherein X' is $-NH_2$, $-NHOH$, $-N(R_4)OH$ or $-NH-NH_2$ wherein $R_4$ has the meaning given for formula I, with the proviso that when X' is $-N(R_4)OH$, $R_6$ is hydrogen; and when required, removing protecting groups at $R_2$ or $R_3$; and b) for the production of a compound of formula I as defined above wherein X is $-NH-N=C(R_4)R_5$, reacting a compound of formula III

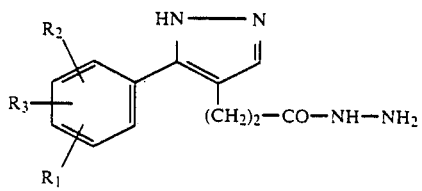

wherein $R_1$, $R_2$ and $R_3$ have the meanings given in relation to formula II with a compound of formula $R_4$—CO—$R_5$, wherein $R_4$ and $R_5$ have the meanings given for formula I, and when required, removing protecting groups at $R_2$ or $R_3$;
and recovering the obtained compound of formula I in free or acid addition salt form.

The above process may be carried out in accordance with standard techniques known in the art.

For process step a), when X' is —$NH_2$, —NH—OH or —NH—$NH_2$, $R_6$ in formula II is conveniently $C_{1-4}$alkyl e.g. ethyl. When reaction is with ammonia (X'=—$NH_2$) this may suitably be carried out in an autoclave e.g. at a temperature of ca. 80° to ca. 200° C. When reaction is with hydroxylamine (X'=—NHOH) the hydroxylamine is conveniently in salt form e.g. in the form of its hydrochloride, and reaction may suitably be carried out in an inert solvent or diluent such as methanol, at a temperature of from e.g. ca. −20° to ca. 10° C., preferably in the presence of an acid binding agent, for example an alkaline metal or alkaline earth metal hydroxide such as KOH. When reaction is with hydrazine (X'=—NH—$NH_2$) this is conveniently in the form of its hydrate, and reaction may suitably be performed in an inert solvent or diluent such as methanol, at a temperature of from e.g. ca. 10° to ca. 180° C. When reaction is with an alkylhydroxylamine (X'=—N(R$_4$)OH) the alkylhydroxylamine is conveniently in salt form, e.g. in the form of its hydrochloride, and reaction may suitably be carried out in an inert solvent or diluent such as tetrahydrofuran, at a temperature of from e.g. ca. −10° to ca. 30° C., preferably in the presence of a dehydrating agent such as dicyclohexylcarbodiimide.

Reaction in accordance with process step b) may suitably be carried out in an inert solvent or diluent such as ethylether, at a temperature of from e.g. 0° C. to reflux, suitably in the presence of a catalyst, for example an aluminium silicate catalyst such as montmorillonite.

When $R_2$ and/or $R_3$ formulae II and III is hydroxy, mercapto or amino this is suitably in protected from. Suitable protecting groups are any of those known in the art. Appropriate hydroxy and mercapto protecting groups are e.g. $C_{1-4}$alkyl and, in particular, benzyl. Suitable amino protecting groups are e.g. t-butyloxy carbonyl and benzoyl. Where such protecting groups are present deprotection may be effected in conventional fashion e.g. in the case of alkyl- or benzyl-protected hydroxy and mercapto groups via ether- or thio-ether-cleavage. Alternatively amino groups as $R_2$ and/or $R_3$ may be obtained by reduction of nitro groups in accordance with conventional procedures.

The compounds of formula I may be recovered from the initially obtained reaction mixture in free or acid addition salt form and initially obtained bases may be converted into acid addition salts and vice versa. Suitable acid addition salts for pharmaceutical application include pharmaceutically acceptable salts with mineral acids such as HCl, for example dihydrochlorides, as well as with organic acids such as maleic acid.

The starting materials of formula III for use in process step b) may be obtained in accordance with process step a). Starting materials of formula II for use in process step a) may be prepared in accordance with conventional techniques for example in accordance with the reaction sequence overleaf.

Step c) may be carried out e.g. by reaction of IV with a compound of formula VIII

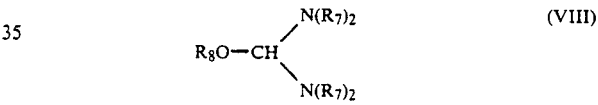

wherein $R_7$ and $R_8$ are each $C_{1-4}$alkyl, for example t.butyloxy-bis-(dimethylamino)-methane [$R_7$=$CH_3$, $R_8$=t.$C_4H_9$], suitably in an inert solvent or diluent, for example toluene, at a temperature of from ca. 10° to ca. 150° C., to yield a compound of formula V$^a$ or (V$^b$).

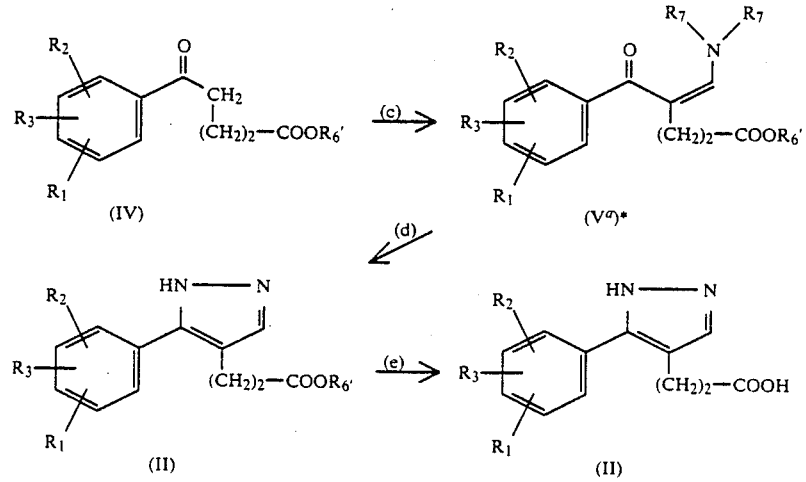

[$R_6'$ and $R_7$ each = $C_{1-4}$alkyl]
*or, when $R_2$ or $R_3$ = hydroxy in the 2-position.

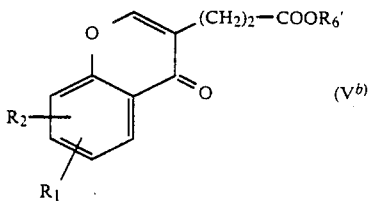

Step d) may be effected by reaction of $V^a$ or $V^b$ with hydrazine, e.g. with hydrazine hydrate, suitably in an inert solvent or diluent, for example ethanol, at a temperature of from ca. −20° to ca. 50° C.

Step e) may be effected by hydrolysis e.g. in an aqueous or aqueous alcoholic medium in the presence of an alkali metal or alkaline earth metal hydroxide at a temperature of e.g. ca. 0° to reflux.

Where it is desired to produce compounds of formula I wherein X is —NH—NH₂, process steps d) and a) above may be carried out as a single reaction proceeding directly from $V^a$ (or $V^b$) to I, i.e. without intervening isolation of the intermediate of formula II, e.g. by reacting $V^a/V^b$ with the appropriate quantity of hydrazine under reaction conditions as hereinbefore described in respect of process step a).

Compounds of formula IV are known (see e.g. Beilstein 10, 708 ff; EI 336 ff, EII 488 ff, EIII 3059 ff), or may be produced analogously to the known compounds e.g. as hereinafter described in examples 1.2. to 8.2.

The following examples are illustrative of the process of the present invention:

EXAMPLE 1

1.1 Preparation of 5-(4-phenoxyphenyl)-1H-pyrazol-4-yl-propionic acid hydrazide [Process step d)+a)]

20 g 4-dimethylaminomethylidene-5-oxo-5-(4-phenoxyphenyl)-pentanoic acid ethyl ester and 12 ml hydrazine hydrate in 160 ml ethanol are heated for 5 hours on an oil bath. The obtained reaction mixture is concentrated under vacuum and shaken with brine and ethyl acetate. The organic phase is extracted 2× with 2N HCl and the aqueous phase rendered alkaline by addition of ammonia and extracted with ethyl acetate. The organic phase is dried over Na₂SO₄ and the solvent evaporated under vacuum. A little ethyl acetate is added to the obtained oil, whereupon the title compound crystallises out as the free base: m.p.=107°–108° C. The dihydrochloride salt may be obtained from the base by dissolving in propan-2-ol adding conc. HCl, followed by crystallisation by addition of ethyl acetate-/ethyl ether: m.p.=118°–120° C.

The following compounds of formula I in which X is —NH—NH₂ may be prepared analogously:

| EXAMPLE | R₁ | R₂ | R₃ | m. p. (°C.) |
|---|---|---|---|---|
| 2.1 | 4-n-C₄H₉— | H | H | 107–108 (Base) |
| 3.1 | 4-n-C₆H₁₃— | H | H | 97–99 (Base) |
| 4.1 | 4-n-C₇H₁₅— | H | H | 105–106 (Base) |
| 5.1 | 4-n-C₈H₁₇— | H | H | 104–105 (Base) |
| 6.1 | 4-phenyl | H | H | 211–212 (Base) |
| 7.1 | 4-n-C₅H₁₁O— | 2-OH | H | 198–200 (2 × HCl) 160–163 (Base) |
| 8.1 | 4-n-C₅H₁₁O— | 2-OH | 3-n-C₅H₁₁O— | 192–194 (Base) |
| 9.1 | 4-n-C₅H₁₁O— | H | H | 115–116 (Base) |
| 10.1 | 4-n-C₅H₁₁O— | 2-OH | 3-OH | 195–197 (Base) |
| 11.1 | 4-n-C₅H₁₁S— | H | H | 129° (Base) |

The starting materials for the above processes are prepared as follows:

1.2 5-Oxo-5(4-phenoxyphenyl)-pentanoic acid ethyl ester 93 g aluminium chloride are added over 15 minutes at −10° C. to a solution of 52.0 g glutaric acid monoethyl ester chloride [Cl—CO—(CH₂)₃—COOC₂H₅]. The mixture is stirred for 15 mins. at 0° to 10° C. and then added portion-wise over a period of 20 mins. at −5° to 10° C. to a pre-prepared solution of 50.0 g diphenylether in 150 ml dichloroethane. The reaction mixture is allowed to rise slowly to room temperature and is then stirred for 12 hours, poured onto ice and shaken well with H₂O/methylene chloride. The organic phase is washed thouroughly with H₂O and saturated NaHCO₃ solution, dried over MgSO₄ and the solvent evaporated off. The obtained light yellow oil is crystallised from hexane/ethyl ether on an ice bath: m.p.=61°–62° C.

The following compounds of formula IV wherein R₆=C₂H₅ are prepared analogously.

| EXAMPLE | R₁ | R₂ | R₃ | Physical Data |
|---|---|---|---|---|
| 2.2 | 4-n-C₄H₉— | H | H | Oil |
| 3.2 | 4-n-C₆H₁₃— | H | H | Oil |
| 4.2 | 4-n-C₇H₁₅— | H | H | Oil |
| 5.2 | 4-n-C₈H₁₇— | H | H | Oil |
| 6.2 | 4-phenyl | H | H | m. p. = 79–80° C. |
| 7.2* | 4-n-C₅H₁₁O— | 2-OH | H | — |
| 8.2 | 4-n-C₅H₁₁O— | 2-OH | 3-n-C₅H₁₁O— | Oil |
| 9.2* | 4-n-C₅H₁₁O— | H | H | Oil |
| 10.2 | 4-n-C₅H₁₁O— | 2-OH | 3-OH | m. p. = 54–57° C. |
| 11.2* | 4-n-C₅H₁₁S— | H | H | m. p. = 54–55° C. |

*Prepared using SnCl₄ in place of AlCl₃.

1.3
4-Dimethylaminomethylidene-5-oxo-5-(4-phenoxyphenyl)-pentanoic acid ethyl ester [Process step c)]

20 g of the product of example 1.2 and 16.7 g t.butyloxy-bis-(dimethylamino)-methane in 250 ml toluene are heated for 20 hours under a nitrogen atmosphere at reflux. The solvent is evaporated off, the residue dissolved in ethyl acetate and filtered over silica gel. The title compound, which is obtained as an oil after evaporation of the solvent, is employed directly in the process of step 1.1, without further purification.

The following compounds of formula V in which each $R_7 = CH_3$ and $R_6 = C_2H_5$ are obtained analogously:

| EXAMPLE | $R_1$ | $R_2$ | $R_3$ |
| --- | --- | --- | --- |
| 2.3 | 4-n-$C_4H_9$— | H | H |
| 3.3 | 4-n-$C_6H_{13}$— | H | H |
| 4.3 | 4-n-$C_7H_{15}$— | H | H |
| 5.3 | 4-n-$C_8H_{17}$— | H | H |
| 6.3 | 4-phenyl | H | H |
| 7.3 | 4-n-$C_5H_{11}O$— | 2-OH | H |
| 8.3 | 4-n-$C_5H_{11}O$— | 2-OH | 3-n-$C_5H_{11}O$— |
| 9.3 | 4-n-$C_5H_{11}O$— | H | H |
| 10.3 | 4-n-$C_5H_{11}O$— | 2-OH | 3-OH |
| 11.3 | 4-n-$C_5H_{11}S$— | H | H |

EXAMPLE 12

12.1 Preparation of
5-(3-hydroxy-1,1'-biphenyl-4-yl)-1H-pyrazol-4-yl-propionic acid hydrazide [Process step a): deprotection]:

3 g of 5-(3-benzyloxy-1,1'-biphenyl-4-yl)-1H-pyrazol-4-yl-propionic acid hydrazide are dissolved with heating in isopropanol and hydrogenated over 10% palladium/charcoal. The catalyst is filtered off, the reaction mixture concentrated by evaporation and the concentrate allowed to stand for ca. 12 hrs. in a refrigerator. The title compound crystallises out as the dihydrochloride and is recovered by filtration: m.p. = 138°-141° C.

The starting material for the above process is prepared as follows:

12.2
5-(3-Benzyloxy-1,1'-biphenyl-4-yl)-5-oxo-pentanoic acid ethyl ester

12.2.1
5-(3-Hydroxy-1,1'-biphenyl-4-yl)-5-oxo-pentanoic acid 24 g aluminium chloride are added at 0° C. to a solution of 10 g glutaric acid anhydride in 300 ml dichloroethane. After stirring for 15 mins. at 0° to 5° C., 15 g 3-methoxy-biphenyl in 50 ml dichloroethane are added rapidly at ca. 0° C. The reaction mixture is stirred for 24 hours at room temperature, poured onto a mixture of ice and conc. HCl and diluted with water. The organic phase is separated off and the aqueous phase extracted 3× with methylene chloride. The combined organic phases are washed thoroughly with water, dried over $MgSO_4$ and clarified with activated charcoal. The solvent is evaporated off and the obtained oil crystallised from ether to yield the title compound: m.p. = 168°-170° C.

12.2.2
5-(3-Hydroxy-1,1'-biphenyl-4-yl)-5-oxo-pentanoic acid ethyl ester 1 ml conc. $H_2SO_4$ are added to a suspension of 5.4 g of the product of example 12.2.1 in 100 ml ethanol. The reaction mixture is heated for 3 hrs. under reflux and concentrated under vacuum. The obtained product is shaken with ice-water and ethyl acetate, the organic phase washed with $H_2O$ and saturated $NaHCO_3$ solution, dried over $MgSO_4$, clarified with activated charcoal and the solvent evaporated off. The title compound is obtained after crystallisation from ethyl ether/hexane: m.p. = 64°-66° C.

12.2.3
5-(3-Benzyloxy-1,1'-biphenyl-4-yl)-5-oxo-pentanoic acid ethyl ester 5 g of the product of example 12.2.2, 2.7 g potassium iodide, 2.3 g potassium carbonate and 2.3 ml benzyl bromide suspended/dissolved in 100 ml absolute dimethylformamide are stirred for 2.5 hrs. at 150° C. The dimethylformamide is evaporated off and the residue shaken with $H_2O$ and ethylacetate, the organic phase washed with $H_2O$, dried over $MgSO_4$, clarified with active charcoal and the solvent evaporated off. The obtained oil is purified chromatographically on silica gel employing toluene/ethyl acetate (20:1) as eluant.

12.3
5-(3-Benzyloxy-1,1'-biphenyl-4-yl)-1H-pyrazol-4-yl-propionic acid hydrazide The title compound is prepared analogously to example 1.1 starting from the product of example 12.2.3: m.p. = 172°-175° C. (2×HCl salt).

EXAMPLE 13

13.1 Preparation of
5-(4-n-hexylphenyl)-1H-pyrazol-4-yl-propionohydroxamic acid [Process step a)]

10 g 5-(4-n-hexylphenyl)-1H-pyrazol-4-yl-propionic acid ethyl ester dissolved in 40 ml methanol are added rapidly to a solution of 4.2 g hydroxylamine hydrochloride and 5 g KOH in 40 ml methanol, pre-cooled to −5° C. After reaching room temperature, the reaction mixture is stirred for 24 hrs. The mixture is filtered and the solvent concentrated under vacuum. The residue is dissolved in ethyl acetate, washed with water, dried with $Na_2SO_4$ and solvent removed by evaporation under vacuum. The title compound is crystallised from ethyl ether/hexane: m.p. = 150°-155° C.

The starting material for the above process is obtained as follows:

13.2 5-(4-n-Hexylphenyl)-1H-pyrazol-4-yl-propionic acid ethyl ester [Process step d)]

9 g of the product of example 3.3 and 2.4 ml hydrazine hydrate in 100 ml ethanol are stirred for 1 hr. at 50° C. The obtained reaction mixture is evaporated carefully under vacuum and purified chromatographically on silica gel using ethyl acetate as eluant.

EXAMPLE 14

Preparation of
5-(4-n-pentyloxyphenyl)-1H-pyrazol-4-yl-propionohydroxamic acid

The title compound is prepared analogously to example 13.1: m.p. = 190°-193° C.

The required starting material, 5-(4-n-pentyloxyphenyl)-1H-pyrazol-4-yl-propionic acid ethyl ester, is obtained from the product of example 9.3 proceeding analogously to example 13.2.

EXAMPLE 15

15.1 Preparation of 5-(4-phenoxyphenyl)-1H-pyrazol-4-yl-propiono-N-methyl-hydroxamic acid [Process step a)]

3.5 g 5-(4-phenoxyphenyl)-1H-pyrazol-4-yl-propionic acid, 1 g N-methyl-hydroxylamine hydrochloride and 1.7 ml triethylamine are dissolved/suspended in 50 ml abs. tetrahydrofuran and 2.3 g dicyclohexylcardodiimide dissolved in a little tetrahydrofuran are added. The reaction mixture is stirred at room temperature until reaction is complete and then immediately filtered. The solvent is evaporated off under vacuum and the residue purified chromatographically using silica gel and ethyl acetate/methanol (15:1) as eluant. The title compound is crystallised from ethyl ether/methylene chloride: m.p. = 118°-120° C.

The starting material for the above process is obtained as follows:

15.2 5-(4-Phenoxyphenyl)-1H-pyrazol-4-yl-propionic acid ethyl ester [Process step d)]

The title compound is obtained analogously to example 13.2 starting from the product of example 1.3.

15.3 5-(4-Phenoxyphenyl)-1H-pyrazol-4-yl-propionic acid [Process step e)]

10 g of the product of example 15.2 and 10 g KOH in 20 ml H$_2$O and 200 ml ethanol are heated under reflux for 2 hrs. The solvent is evaporated off and the residue treated with 2N HCl whereupon the title compound precipitates out and is recovered by filtration: m.p. = 195°-198° C.

EXAMPLE 16

Preparation of
5-(4-n-pentoxyphenyl)-1H-pyrazol-4-yl-propiono-N-methyl-hydroxamic acid The title compound is prepared analogously to example 15.1: m.p. = 150°-152° C.

The required starting material is prepared from the product of example 9.3, proceeding analogously to examples 13.2 and 15.3.

EXAMPLE 17

Preparation of
5-(4-hexylphenyl)-1H-pyrazol-4-yl-propionic acid amide [Process step a)]

7.5 g of the product of example 13.2 in concentrated ammonia solution are stirred in an autoclave for 27 hrs. at 150° C. The product mixture is shaken with H$_2$O/ethyl acetate. The organic phase is dried with Na$_2$SO$_4$, the solvent evaporated off and the residue purified chromatographically on silica gel using ethyl acetate/methanol (20:1) as eluant. The title compound is crystallised from a little methylene chloride: m.p. = 127°-130° C.

EXAMPLE 18

Preparation of
5-(4-hexylphenyl)-1H-pyrazol-4-yl-propanoic acid 2-(1-methyl-ethylidene)-hydrazide [Process step b): X in formula I = —NH—N=C(CH$_3$)$_2$]:

6 g of the product of example 3.1 are dissolved in 20 ml acetone and 30 ml ether. 5 g 4 Å molecular seive and ca. 3 g montmorrillonite K 10 katalyst obtainable from the company Südchemie A.G., Munich are added and the reaction mixture is stirred for 48 hours at room temperature. Insoluble components are filtered off and the solvent evaporated off. The title compound is crystallised from hexane in the presence of a little methanol: m.p. 143°-145° C.

The compounds of formula I as well as their pharmaceutically acceptable acid addition salts (referred to herein as compounds of the invention) exhibit pharmacological activity and are therefore indicated for use as pharmaceutical agents, e.g. for therapy. In particular they possess lipoxygenase inhibiting activity as can be shown in standard pharmacological tests for example in accordance with the following lipoxygenase assay:

Human neutrophils are isolated from normal donor blood (buffy coats) by dextran sedimentation, hypotonic lysis of contaminating erythrocytes and several washes in saline. $3.5 \times 10^7$ cells/ml in PBS are preincubated at 37° C. in the presence of test substance or solvent (control) for 5 min. Calcium ionophore A23187 (20 μM) is then added and incubation continued for 2 min before addition of [1-$^{14}$C]-arachidonic acid (0.11 mM) and further incubation for 4 min. The reaction is terminated by addition of 2 vol of methanol followed by centrifugation. The supernatant is acidified to pH 3. The products are extracted into diethyl ether, and are then separated by thin layer chromatography using the organic phase of ethyl acetate: 2,2,4-trimethyl pentane: acetic acid: water (110:50:20:100, v/v) as the solvent system. The radioactive spots are located by radio-scanning and quantified by liquid scintillation counting (see Bougeat and Samuelsson, Proc. Nat. Acad. Sci. 76, 2148-2152, 1979 and Jakschik et al., Prostaglandins 20, 401-410, 1980).

Determined IC$_{50}$ (concentrated at which 50% inhibition is achieved compared with control) for compounds of the invention in the above assay are of the order of from $1 \times 10^{-5}$ to $1 \times 10^{-7}$ mol/liter. Thus a determined IC$_{50}$ for the compound of Example 1.1 is $3 \times 10^{-7}$ mol/liter.

The compounds of the invention are accordingly useful for the treatment of disorders in which endogenous products of the lipoxygenase pathway, for example leukotrienes such as leukotriene C, play a direct or indirect pathophysiological role, for example for the treatment or prophylaxis of asthma (e.g. as bronchospasmolytic agents), as well as for the treatment of inflammation, and, in particular, for the treatment of psoriasis, inflammatory skin conditions, inflammatory bowel syndrome, ulcerative colitis, antigen-induced inflammatory reactions.

For the above uses the required dosage will of course vary, depending on the mode of administration, the particular condition to be treated and the therapy desired. In general however, satisfactory results are obtained on administration of compounds of the invention at a daily dosage of from about 0.15 to about 2.5 mg/kg body weight administered e.g. i.v. in divided doses 2 to 4×a day or in retard form.

For larger mammals the total daily dosage is in the range of from about 10 to about 200 mg and suitable unit dosage forms, e.g. for i.v. administration, comprise from about 2.5 to about 100 mg of compound of the invention, or in sustained release form.

The compounds of the invention may be administered by any conventional route, for example parenterally, e.g. in form of injectable solutions or suspensions, enterally, e.g. orally, e.g. in the form of tablets or capsules, or in a nasal, suppository or topical form.

For use in the treatment of psoriasis and other inflammatory skin diseases, the compounds of the invention may appropriately be applied topically, e.g. to areas of the skin exhibiting psoriatic lesion, at regular intervals, e.g. 1, 2 or 3×daily. For the purpose of topical application the compounds of the invention may be put up in the form of an ointment, gel, cream, lotion or like suitable for topical application and comprising the compound of the invention together with one or more, carriers or diluents acceptable for dermal application.

Compound of Examples 1.1, 3.1 and 9.1 are preferred.

The compounds of formula I may be administered in free form or in pharmaceutically acceptable salt form. Such salts exhibit the same order of activity as the free compounds.

In accordance with the foregoing the present invention also provides:

i) A compound of formula I or pharmaceutically acceptable acid addition salt thereof, for use as a pharmaceutical, e.g. for use as an anti-asthma or asthma-prophylactic agent or for use as an anti-inflammatory agent particularly in the treatment of psoriasis, or inflammatory skin or bowel conditions, e.g. as defined above;

ii) A method for the treatment or prophylaxis of asthma or for the treatment of inflammation, e.g. diseases or conditions as defined above, particularly of psoriasis, in a subject in need of such treatment, which method comprises administering to said subject an effective amount of a compound of formula I or pharmaceutically acceptable acid addition salt thereof; as well as iii) A pharmaceutical composition comprising a compound of formula I or pharmaceutically acceptable acid addition salt thereof, together with pharmaceutically acceptable diluent or carrier therefor.

The pharmaceutical compositions of the invention may be prepared in conventional manner. They may for example be prepared by by bringing a compound of formula I, in free form or in pharmaceutically acceptable salt form, into intimate admixture with the pharmaceutically acceptable diluents or carriers and effecting formulation or presentation so as to provide for or permit administration.

What is claimed is:

1. A compound of formula I

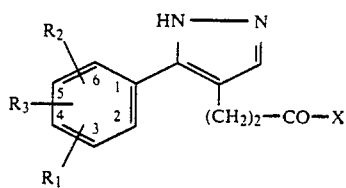

(I)

wherein
$R_1$ is alkyl, alkoxy, alkylthio, alkylamino, aryl, aryloxy, arylthio, arylamino, aralkyl, aralkoxy, aralkylthio or aralkylamino, $R_2$ and $R_3$ are each independently hydrogen, halogen, hydroxy, mercapto, nitro or amino or have the meanings given for $R_1$, and X is $-NH-NH_2$ or $-NH-N=C(R_4)R_5$, wherein $R_4$ and $R_5$ are each alkyl, or acid addition salt thereof.

2. A compound according to claim 1 wherein $R_1$ is $C_{1-12}$alkyl, $C_{1-12}$alkoxy, $C_{1-12}$alkylthio, phenyl or phenoxy.

3. A compound according to claim 1 wherein $R_2$ and $R_3$ are each independently hydrogen, hydroxy or $C_{1-4}$alkoxy.

4. A compound according to claim 1 wherein $R_4$ and $R_5$ are each $C_{1-4}$alkyl.

5. A compound according to claim 1 selected from the group consisting of:

5-(4-phenoxyphenyl)-1H-pyrazol-4-yl-propionic acid hydrazide;

5-(4-n-butylphenyl)-1H-pyrazol-4-yl-propionic acid hydrazide;

5-(4-n-heptylphenyl)-1H-pyrazol-4-yl-propionic acid hydrazide;

5-(4-n-octylphenyl)-1H-pyrazol-4-yl-propionic acid hydrazide;

5-(1,1'-biphenyl-4-yl)-1H-pyrazol-4-yl-propionic acid hydrazide;

5-(4-n-pentoxy-2-hydroxy-phenyl)-1H-pyrazol-4-yl-propionic acid hydrazide;

5-(3,4-di-n-pentoxy-2-hydroxy-phenyl)-1H-pyrazol-4-yl-propionic acid hydrazide;

5-(4-n-pentoxy-2,3-dihydroxy-phenyl)-1H-pyrazol-4-yl-propionic acid hydrazide;

5-(4-n-pentylthio-phenyl)-1H-pyrazol-4-yl-propionic acid hydrazide;

5-(3-hydroxy-1,1'-biphenyl-4-yl)-1H-pyrazol-4-yl-propionic acid hydrazide;

5-(4-hexylphenyl)-1H-pyrazol-4-yl-propanoic acid 2-(1-methyl-ethylidene)-hydrazide;

and acid addition salts therof.

6. 5-(4-n-hexylphenyl)-1H-pyrazol-4-yl-propionic acid hydrazide and acid addition salts thereof.

7. 5-(4-n-pentoxyphenyl)-1H-pyrazol-4-yl-propionic acid hydrazide and acid addition salts thereof.

8. A pharmaceutical composition comprising a compound according to claim 1 or pharmaceutically acceptable acid addition salt thereof, together with a pharmaceutically acceptable diluent or carrier therefor.

9. A pharmaceutical composition according to claim 8 for topical application.

10. A method for the treatment or prophylaxis of asthma or for the treatment of inflammation in a subject in need of such treatment, which method comprises administering to said subject an effective amount of a compound of formula I as defined in claim 1, or pharmaceutically acceptable acid addition salt thereof.

11. A method for the treatment of psoriasis, inflammatory skin conditions, inflammatory bowel syndrome, ulcerative colitis, or antigen-induced inflammatory reactions in a subject in need of such treatment, which method comprises administering to said subject an effective amount of a compound of formula I as defined in claim 1, or pharmaceutically acceptable acid addition salt thereof.

* * * * *